(12) United States Patent
Eskuri et al.

(10) Patent No.: US 8,282,599 B2
(45) Date of Patent: Oct. 9, 2012

(54) THERAPEUTIC CATHETER WITH DISPLACEMENT SENSING TRANSDUCER

(75) Inventors: Alan Eskuri, Hanover, MN (US); Daniel Lafontaine, Plymouth, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1029 days.

(21) Appl. No.: 11/941,472

(22) Filed: Nov. 16, 2007

(65) Prior Publication Data

US 2008/0140006 A1 Jun. 12, 2008

Related U.S. Application Data

(60) Provisional application No. 60/873,598, filed on Dec. 8, 2006.

(51) Int. Cl.
*A61M 25/095* (2006.01)
(52) U.S. Cl. .......................... 604/117; 604/20
(58) Field of Classification Search .............. 604/20, 604/65, 117
See application file for complete search history.

(56) References Cited

U.S. PATENT DOCUMENTS

| | | | | |
|---|---|---|---|---|
| 4,411,648 | A | * | 10/1983 | Davis et al. ............ 604/21 |
| 4,697,144 | A | | 9/1987 | Howbrook |
| 4,750,489 | A | * | 6/1988 | Berkman et al. ........ 606/166 |
| 5,080,103 | A | * | 1/1992 | Olivier .................. 600/461 |
| 5,313,160 | A | | 5/1994 | Gloden et al. |
| 5,607,462 | A | | 3/1997 | Imran |
| 5,916,229 | A | * | 6/1999 | Evans .................... 606/171 |
| 6,102,926 | A | | 8/2000 | Tartaglia et al. |
| 6,251,121 | B1 | | 6/2001 | Saadat |
| 6,309,370 | B1 | | 10/2001 | Haim et al. |
| 6,951,549 | B1 | | 10/2005 | Beyerlein |
| 2003/0130615 | A1 | * | 7/2003 | Tom .................... 604/65 |
| 2004/0049219 | A1 | * | 3/2004 | Briggs et al. ............ 606/181 |
| 2004/0049231 | A1 | * | 3/2004 | Hafer .................. 607/3 |
| 2004/0260240 | A1 | | 12/2004 | Beyerlein |

FOREIGN PATENT DOCUMENTS

GB 2335990 A 10/1999

OTHER PUBLICATIONS

Yuqing Lai: "Eddy Current Displacement Sensor with LTCC Technology" [Online] Jun. 30, 2006, Albert-Ludwigs Universitat Freiburg IM Breisgau, Freiburg, Germany, XP002480149, Retrieved from the Internet: URL:htttp://www.imtek.de/content/pdf/public/2005/dissertation-lai.pdf> [retrieved on May 14, 2008] Chapter "2.2 Conventional displacement sensors".
Brandao Faria Ja: "A new magnetic displacement sensor and linear actuator device" Journal of Applied Physics, American Institute of Physics. New York, US, vol. 87, No. 9 May 1, 2000, pp. 7076-7078, XP012050735 ISSN: 0021-8979 abstract.

* cited by examiner

*Primary Examiner* — Nicholas Lucchesi
*Assistant Examiner* — Gerald Landry, II
(74) *Attorney, Agent, or Firm* — Vidas, Arrettt and Steinkraus

(57) ABSTRACT

A catheter device having a proboscis, such as a needle, and a transducer which detects the axial displacement of the proboscis in relation to the distal tip of the catheter. The transducer is positioned at a distal portion of the catheter and may comprise an induction coil or a potentiometer. Axial displacement of the proboscis changes the amount of inductance or resistance in the transducer. This change in inductance or resistance can be calibrated to the amount of axial displacement of the proboscis and provided as feedback to the user.

23 Claims, 8 Drawing Sheets

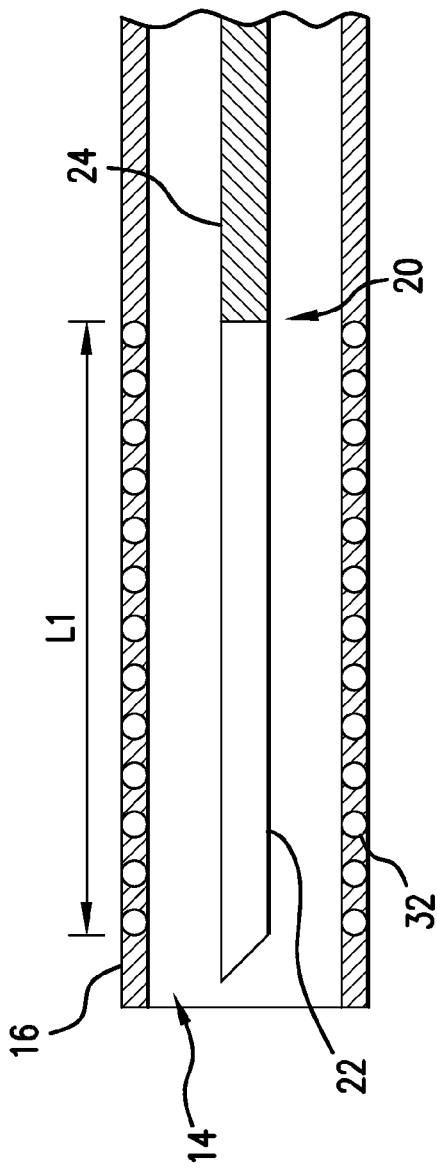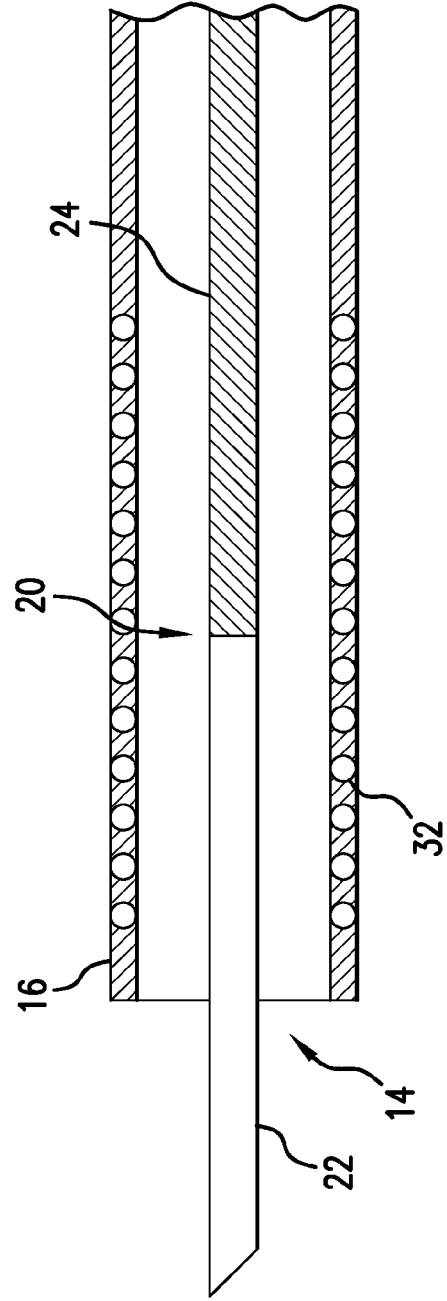

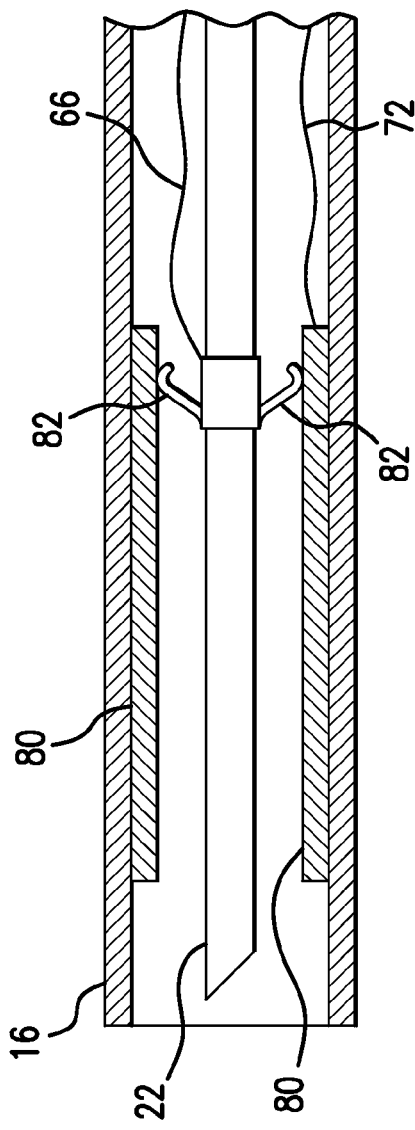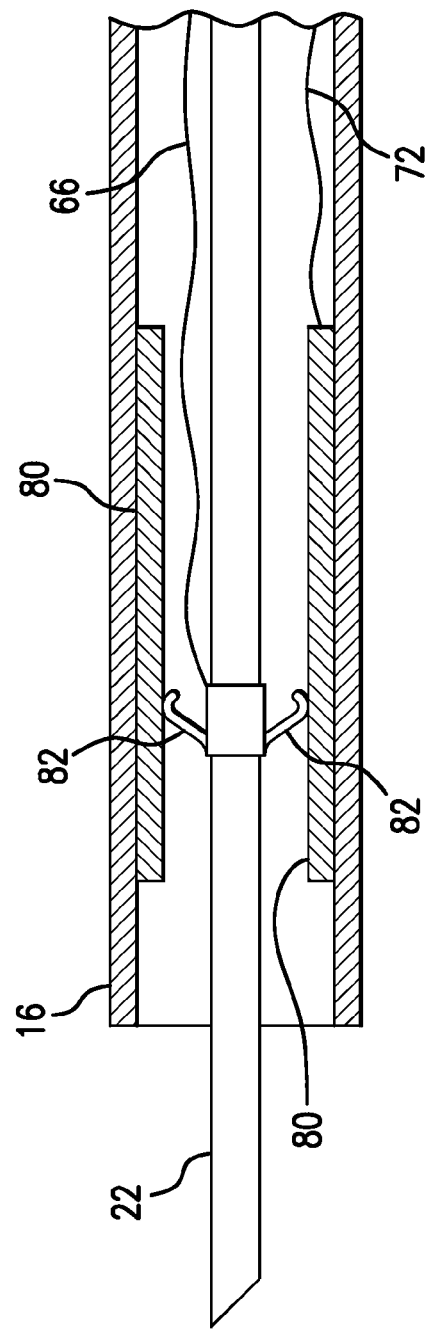

THERAPEUTIC CATHETER WITH DISPLACEMENT SENSING TRANSDUCER

RELATED APPLICATIONS

This application claims benefit of U.S. Provisional Application No. 60/873,598, filed Dec. 8, 2006, which is incorporated herein in its entirety.

TECHNICAL FIELD

The present invention relates to medical devices, more particularly, to therapeutic catheters.

BACKGROUND

Catheters are used in a wide variety of minimally-invasive or percutaneous medical procedures. One type of catheter is an intravascular catheter, which enables a physician to remotely perform a medical procedure by inserting the catheter into the vascular system of the patient at an easily accessible location and navigating the tip of the catheter to the target site. Using catheter-based methods, many internal sites may be remotely accessed through the patient's vascular system or other body lumen structure.

In some applications, a needle may be connected to a catheter assembly to deliver a therapeutic agent into remote sites within a patient's body. For example, in a percutaneous myocardial revascularization procedure, the inside surface of the heart is accessed by an intravascular catheter via a retrograde route through the venous system. A needle is advanced through the catheter, and the heart muscle is then injected with therapeutic agents, such as stem cells or drugs, to promote new blood vessel formation in the heart muscle.

When using an injection catheter, the depth of needle penetration into the tissue is important because the therapeutic agent may require delivery at a precise depth and/or because excess needle penetration may cause injury to the tissue. However, because the needle is not visible to the physician, it can be difficult to determine the penetration depth of the needle. In some cases, the physician can estimate the penetration depth of the needle by the distance the needle has been advanced through the catheter. However, when the catheter takes a tortuous path through the vascular system, for various reasons related to the bending and curving of the catheter, the distance in which the needle has been advanced proximally is not necessarily equal to the distance the needle has traveled from the distal tip of the catheter. Therefore, it is desirable to provide feedback that indicates the actual distance in which the needle has been advanced from the distal tip of the catheter.

SUMMARY OF THE INVENTION

The present invention provides a catheter device having a proboscis assembly with a transducer at a distal portion of the catheter that measures the axial displacement of the proboscis assembly. In certain embodiments, the present invention provides a catheter device having a proximal end and a distal end, wherein the catheter comprises an elongated hollow housing at the distal end; a proboscis assembly disposed within the housing, wherein the proboscis assembly has a central axis and is axially movable relative to the hollow housing; and a transducer for measuring axial displacement of the proboscis assembly relative to the hollow housing, wherein the transducer comprises an induction coil. The catheter device is designed such that axial displacement of the proboscis assembly changes the amount of inductance in the induction coil. The change in inductance can be calibrated to the axial displacement of the proboscis assembly and provided as feedback to the user.

In certain embodiments, a catheter device of the present invention has a transducer which comprises a potentiometer. The catheter device is designed such that axial displacement of the proboscis assembly changes the amount of resistance through the potentiometer. The change in resistance can be calibrated to the axial displacement of the proboscis assembly and provided as feedback to the user.

In certain embodiments, the present invention provides a method of using a catheter device having a proboscis assembly and a transducer that measures the axial displacement of the proboscis assembly.

BRIEF DESCRIPTION OF THE DRAWINGS

FIGS. 3A and 3B are cross-section side views of the catheter device of FIG. 2.

FIGS. 9A and 9B are cross-section side views of a catheter device according to yet another embodiment.

DETAILED DESCRIPTION

A catheter device of the present invention comprises a catheter having a proboscis and a transducer which measures the axial displacement of the proboscis at the distal end of the catheter. As used herein, the term "proboscis" refers to an elongate structure that protrudes from the distal opening of the catheter to provide and/or deliver a diagnostic or therapeutic intervention. Examples of proboscis include needles; electrodes; sensors; probes including those used for applying RF or microwave therapy, cryotherapy, or ultrasound; or optical fibers (e.g., for use in sensing, imaging, phototherapy, or laser ablation therapy, such as in transmyocardial revascularization). The proboscis may include components that are used in catheter-based interventions, such as balloons, stents, blades, hooks, needles, or ports. The proboscis may include mechanisms for delivering catheter-based interventions, including mechanisms for grasping, incising, cutting, penetrating, delivering therapeutic agents, or delivering implants or capsules. Depending upon the particular application, the proboscis may have any of various configurations or characteristics; for example, the proboscis may be flexible or rigid, curved or straight, hollow or solid, sharp or blunt.

In certain embodiments, a catheter device of the present invention comprises a catheter having an induction coil at a distal portion of the catheter. The induction coil may be formed of a wire winding and may be made of any electrically conductive material, such as aluminum, gold, silver, copper, stainless steel, nitinol, or conductive polymer. A varying electric current is passed through the induction coil to produce inductance in the coil. The varying current flow may be of any waveform, including sinusoidal AC or pulsed DC.

In this embodiment, the catheter device further comprises a sheath at a distal portion of the catheter, wherein a proboscis assembly is slidably disposed within the sheath. The proboscis assembly comprises a proboscis (e.g., a needle for use in penetrating tissue and/or delivering a therapeutic agent). At least a portion of the proboscis assembly is formed of a ferromagnetic material, such as stainless steel, nitinol, etc. The proboscis assembly is axially aligned with the induction coil such that the proboscis assembly is capable of serving as a core for the induction coil.

Figure 1:
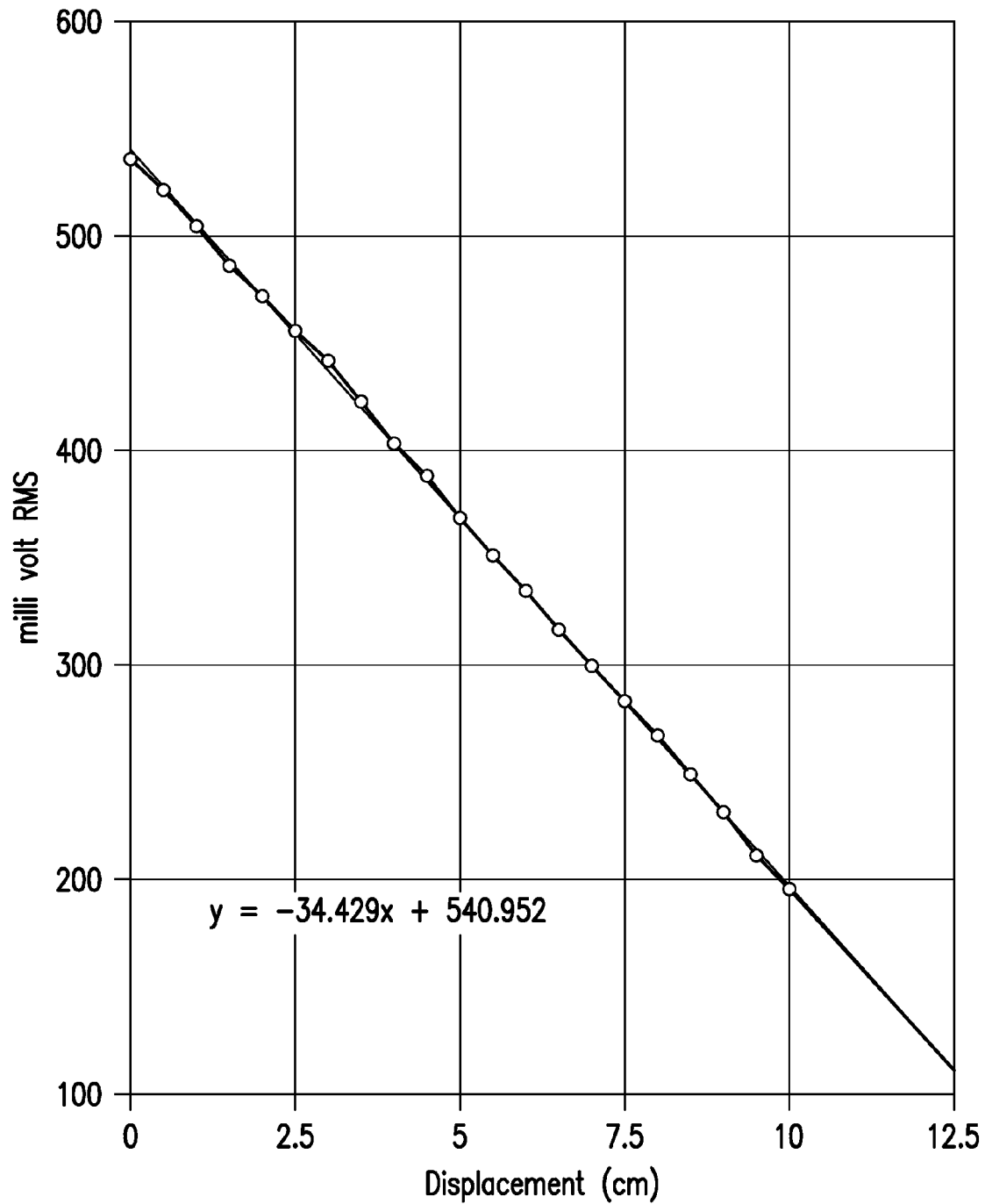
FIG. 1 is a graph demonstrating the relationship between axial displacement of a ferromagnetic core in an induction coil and the resulting inductive reactance in the coil.

One of the factors that determines the amount of inductance in an induction coil is the magnetic permeability of the core. A coil can be made to have variable inductance by sliding a ferromagnetic core into and out of the coil, which changes the effective permeability within the coil. This method of permeability tuning can be demonstrated in FIG. 1, where a stainless steel core is introduced into a 1000 turn induction coil over a distance of 10 cm. Using a conventional induction sensor circuit and a 100 kHz AC signal, the change in inductive reactance (determined by the change in RMS voltage) is measured and is shown to be linearly proportional to the displacement of the ferromagnetic core. Thus, in this embodiment of the present invention, the proboscis assembly is designed so that axial displacement of the proboscis assembly in relation to the induction coil will vary the magnetic permeability of the core. This results in a change in the inductance in the coil, which can be measured using any of various induction sensing circuits known in the art, such as a circuit that measures the amount of inductive reactance.

Figure 2:
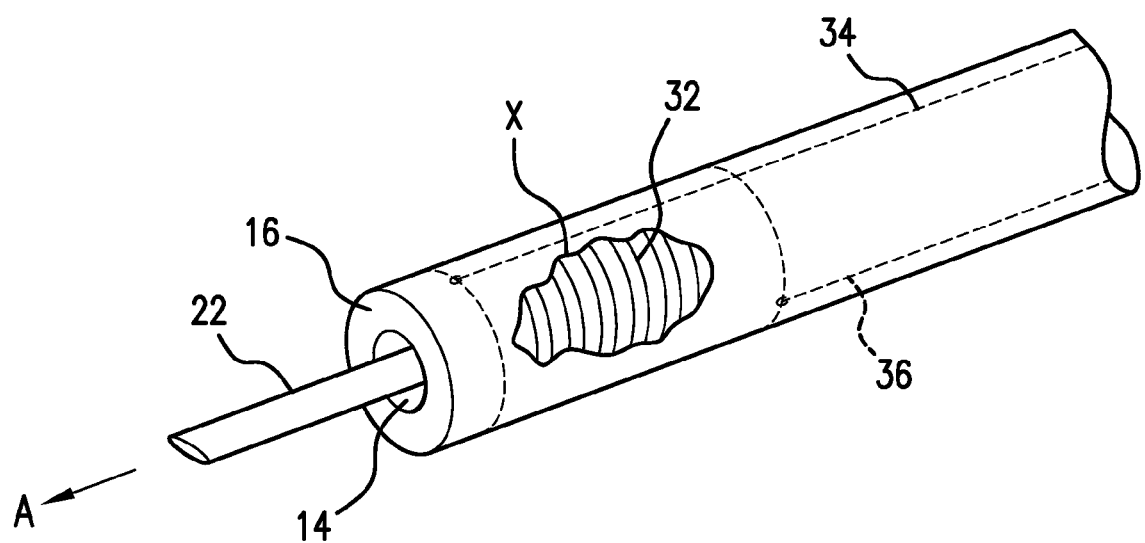
FIG. 2 is a perspective view of the distal portion of a catheter device according to an embodiment of the present invention.
Figure 4:
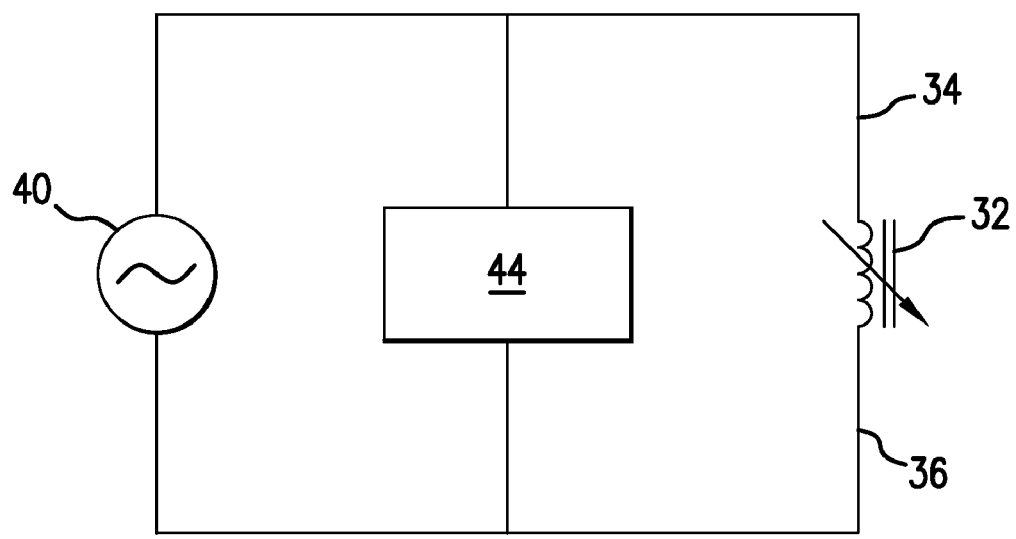
FIG. 4 is a circuit diagram showing an induction coil according to certain embodiments of the present invention.

The following non-limiting examples further illustrate the present invention. In an embodiment as shown in FIGS. 2, 3A, and 3B, a catheter device of the present invention comprises a needle sheath 16 and a distal opening 14 at the distal tip of the catheter device. An induction coil 32 (shown through cut-away X in FIG. 2) is incorporated within the thickness of needle sheath 16. Referring to FIGS. 2 and 4, electrical leads 34 and 36 are coupled to the terminal ends of induction coil 32 to form a circuit with an AC signal source 40 and an induction sensor 44.

The catheter device further comprises a needle assembly 20 slidably disposed within needle sheath 16 and in axial alignment with induction coil 32. Needle assembly 20 comprises a hollow, bevel-tipped injection needle 22 having a central axis A and a needle mounting 24. Needle 22 may be advanced distally or retracted proximally within needle sheath 16. In FIG. 3A, the catheter device is shown in one configuration where needle 22 is retracted within needle sheath 16. In FIG. 3B, the catheter device is shown in another configuration where needle 22 is extended out of the distal opening 14 of the catheter device. The length of needle 22 will vary according to the specific clinical application. For certain applications, the length of needle 22 may range from 5 mm to 10 cm. In this embodiment, length L1 of induction coil 32 corresponds to the length of needle 22. However, other lengths for induction coil 32 are possible, which may be shorter or longer than needle 22.

In this embodiment, needle 22 is made of any ferromagnetic material while mounting 24 is made of any material which has different magnetic permeability than the material in which needle 22 is made. For example, needle 22 may be made of stainless steel and mounting 24 may be made of a non-ferromagnetic material, such as a polymeric material.

Axial movement of needle 22, proximally or distally, will change the ferromagnetic core of induction coil 32. For example, as needle 22 in the retracted position shown in FIG. 3A is advanced distally to the extended position as shown in FIG. 3B, stainless steel needle 22 begins to exit induction coil 32 and non-ferromagnetic mounting 24 begins to enter induction coil 32. This reduces the amount of induction in induction coil 32, which is measured by induction sensor 44. The amount of change in the inductance can then be calibrated to the displacement of needle 22 relative to needle sheath 16 and provided as feedback to the user.

The present invention also contemplates alternate embodiments of the proboscis assembly such that axial displacement of the proboscis assembly will vary the ferromagnetic core of the induction coil. This is achieved by designing the proboscis assembly to have at least one distal portion with a different magnetic permeability than at least one proximal portion. For example, a distal portion of the proboscis assembly may be made of a ferromagnetic material (which has a relatively higher permeability), while a proximal portion of the proboscis assembly is made of a non-ferromagnetic material (which has a relatively lower permeability).

Figure 6:
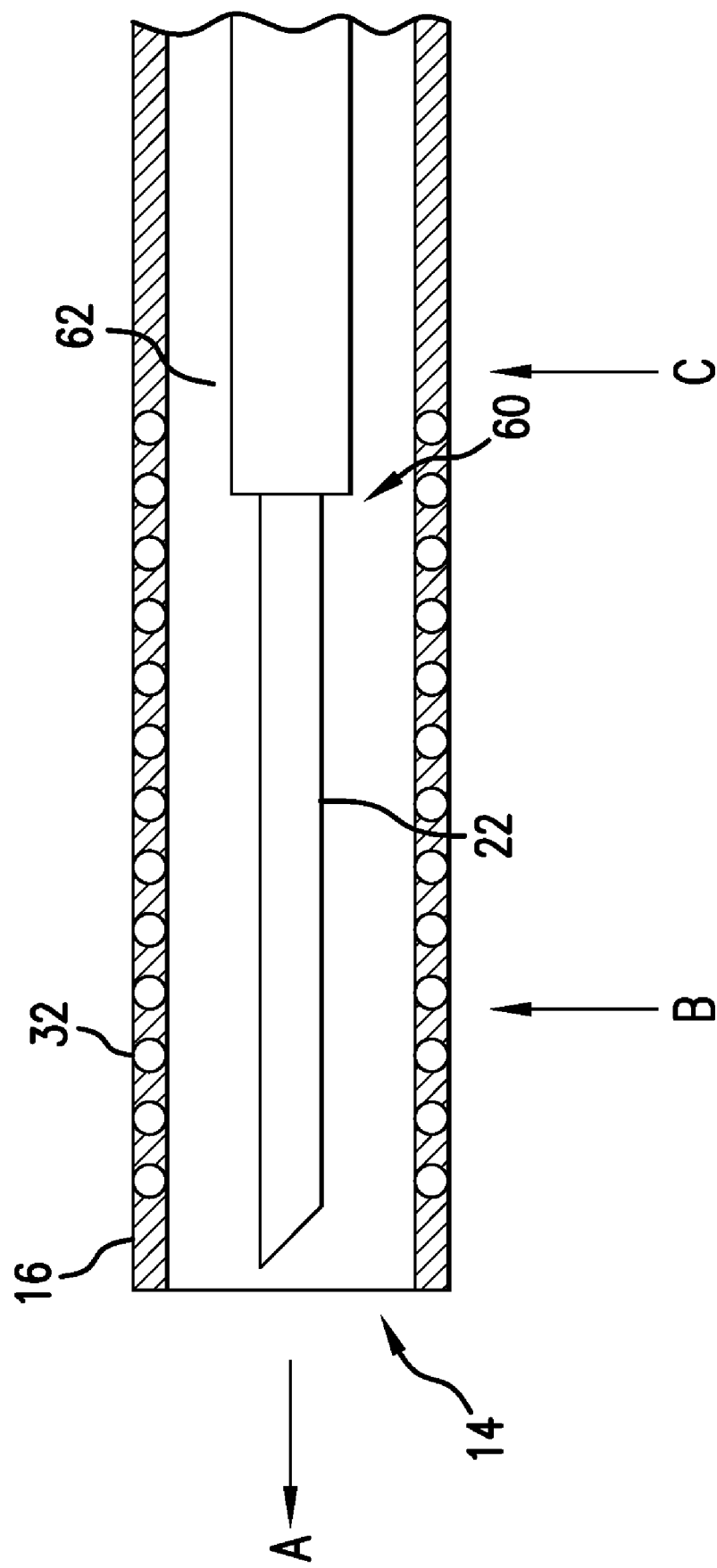
FIG. 6 is a cross-section side view of a catheter device according to another embodiment.

In another embodiment as shown in FIG. 6, a needle assembly 60 comprises a mounting 62 formed of the same material as needle 22 (e.g., stainless steel). Arrows B and C represent planes that are orthogonal to central axis A and intersecting needle 22 and mounting 62, respectively. The cross-sectional diameter of mounting 62 (at plane C) is greater than that of needle 22 (at plane B). As needle assembly 60 is advanced distally, mounting 62 enters induction coil 32, increasing the ferromagnetic core and causing an increase in inductance.

Figure 7A:
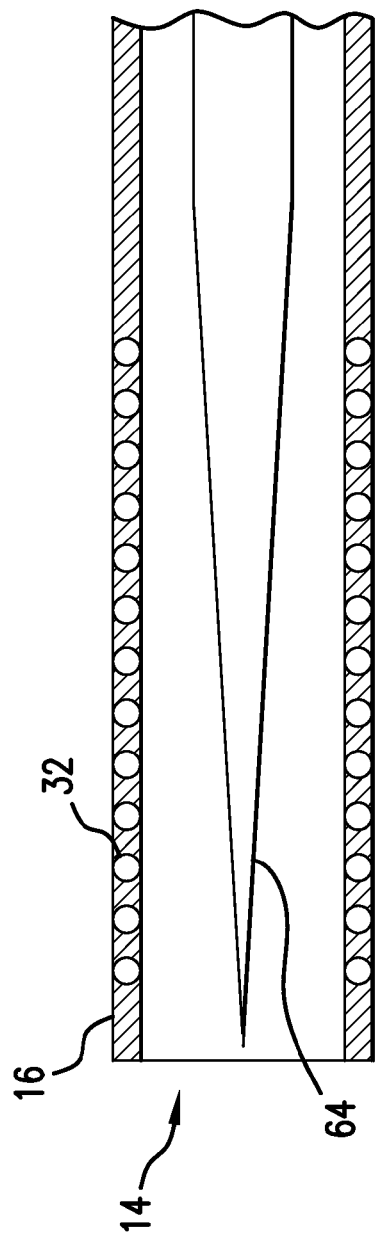
FIGS. 7A and 7B are cross-section side views of a catheter device according to yet another embodiment.
Figure 7B:
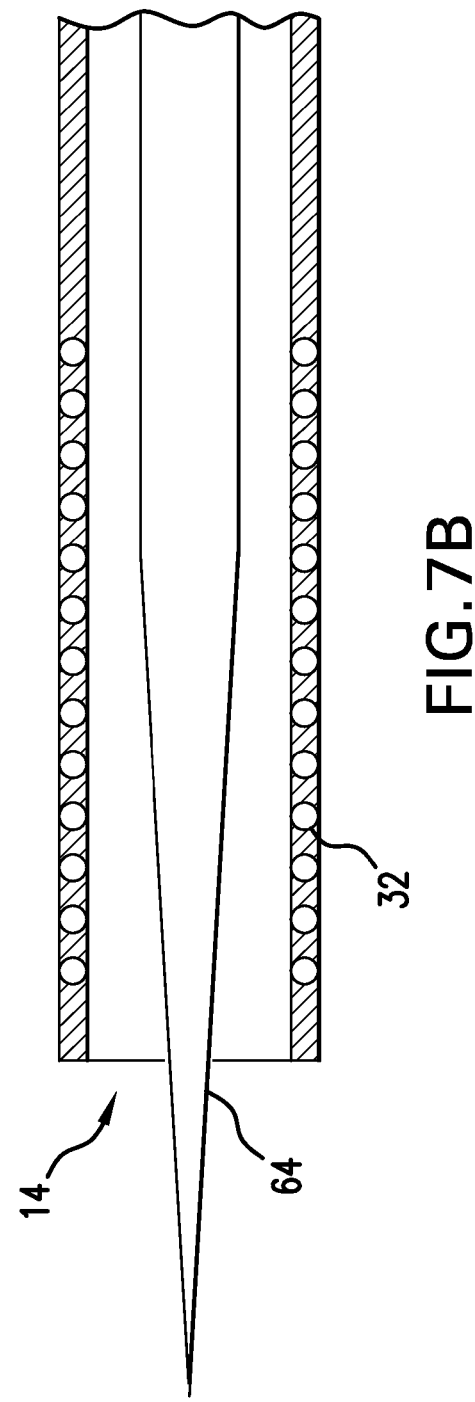

In yet another embodiment as shown in FIGS. 7A and 7B, a catheter device may use a tapered needle 64 having a conical shape with a pencil-point. As tapered needle 64 is advanced distally, the amount of ferromagnetic material in the core of induction coil 32 increases, causing an increase in inductance.

In certain embodiments, a catheter device of the present invention comprises a catheter having a potentiometer at a distal portion of the catheter. The potentiometer comprises a resistor element made of any conventional resistor material and in the form of a strip, coil, or any other configuration suitable for use in the distal portion of a catheter.

In this embodiment, the catheter device further comprises a sheath at a distal portion of the catheter, wherein a proboscis assembly is slidably disposed within the sheath. The proboscis assembly comprises a proboscis and a potentiometer wiper attached to the proboscis assembly. The wiper is made of an electrically conductive material and is in electrical and mechanical contact with the resistor element. The resistor element and wiper are joined in an electrical circuit with any suitable source of electric current. In this manner, the proboscis assembly, wiper, and resistor element combine to form a potentiometer. Axial movement of the proboscis assembly changes the wiper's contact point on the resistor element, thus changing the amount of resistance through the resistor element. The change in the resistance is measured using any conventional resistance sensing circuit and is correlated to the axial displacement of the proboscis assembly. Within certain embodiments, the resistor element is designed so that the resistance is linearly proportional to the position of the wiper. For example, the composition, density, and shape of the resistor element may be constant throughout.

Figure 8A:
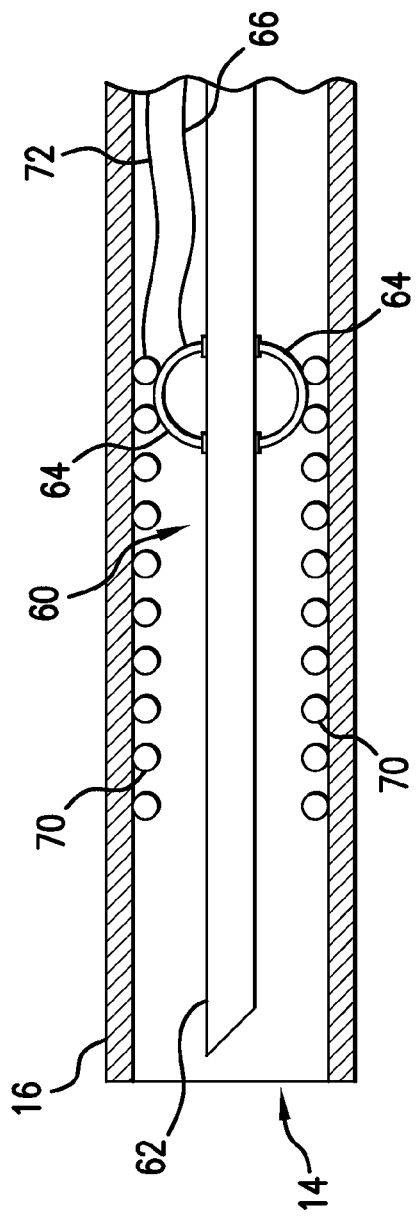
FIGS. 8A and 8B are cross-section side views of a catheter device according to yet another embodiment.
Figure 8B:
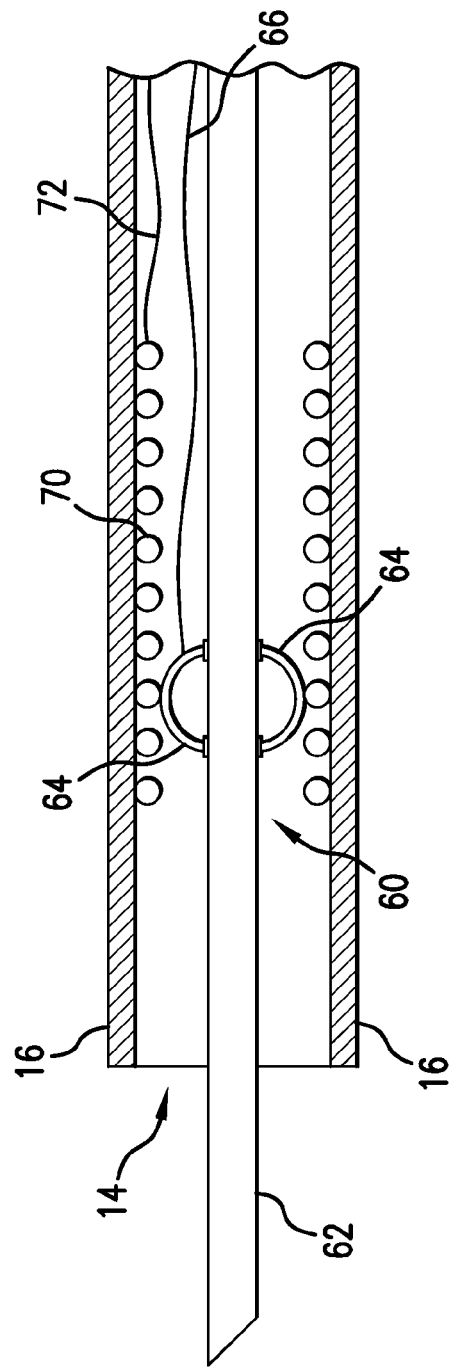

The following non-limiting examples further illustrate the present invention. In an embodiment as shown in FIGS. 8A and 8B, a catheter device comprises a needle sheath 16 and a distal opening 14 at the distal tip of the catheter device. A helical coil 70 of resistance wire is positioned on the inner surface of needle sheath 16.

Figure 5:
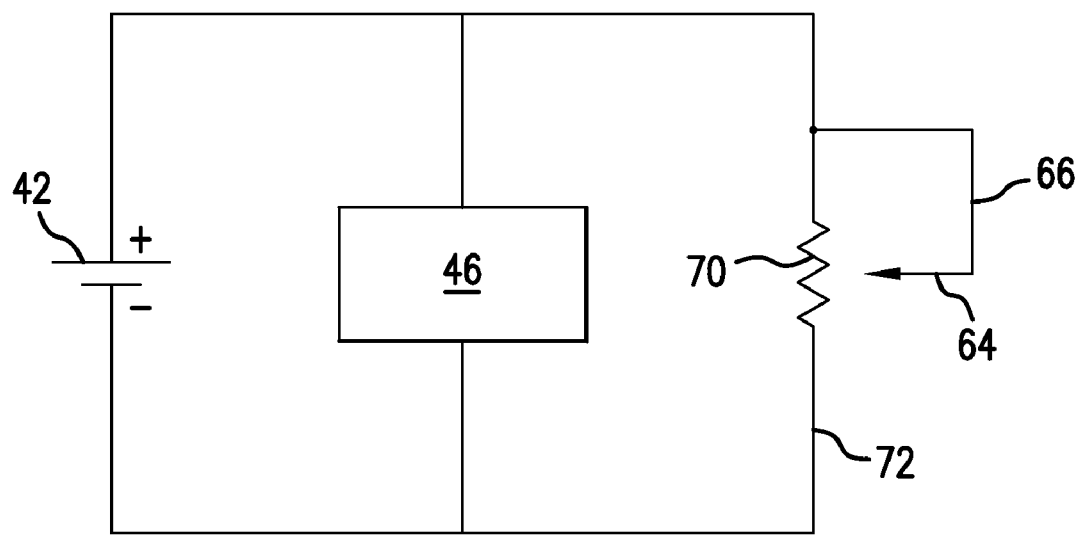
FIG. 5 is a circuit diagram showing a potentiometer according to certain embodiments.

The catheter device further comprises a needle assembly 60 slidably disposed within needle sheath 16. Needle assembly 60 comprises a needle 62 and a leaf-type spring 64 formed of an electrically conductive material. Spring 64 is in mechanical and electrical contact with helical coil 70 and serves as a potentiometer wiper. The proximal terminal end of helical coil 70 is coupled to a lead 72 and spring 64 is coupled to a lead 66. As shown in FIG. 5, helical coil 70, spring 64, and leads 72 and 66, are joined in a circuit with an electrical current source 42 and a resistance sensor 46 (e.g., an ohmeter).

FIG. 8A shows needle 62 in a retracted position, and FIG. 8B shows needle 62 in an extended position. As demonstrated in these figures, axial movement of needle assembly 60 causes leaf-type spring 64 to slide along helical coil 70 so that varying lengths of helical coil 70 are included in the electrical circuit. This results in varying amounts of resistance through helical coil 70 in linear proportion to the amount of axial displacement of needle assembly 60. The varying amounts of resistance can be measured using any conventional means, such as an ohmeter, which can be calibrated to the axial displacement of needle 62 and provided as feedback to the user.

The present invention contemplates other configurations for the resistor element and/or wiper. For example, in an alternate embodiment, as shown in FIGS. 9A and 9B, the resistor element is a resistor strip 80 (which, in this embodiment, extends circumferentially around the inner diameter of needle sheath 16). This embodiment also demonstrates an alternate shape for a wiper element, shown here as a leaf-spring 82. In other alternate embodiments, the resistor element may be a coil of electrically conductive ink printed on the inner surface of needle sheath 16 or an electrically conductive polymer. In some embodiments, needle sheath 16 itself may be made of an electrically conductive polymer and function as the resistor element.

In addition to functioning as a transducer, the induction coil or the resistor element may also serve a structural function in the catheter device. Where the proboscis is a needle, the needle can be any needle for penetrating tissue and/or delivering therapeutic agents, including needles that are hollow bore or solid bore, needles that are straight, curved, or corkscrew-shaped, and electrode needles. The proboscis and/or proboscis assembly may be actuated by any mechanism known in the art.

The catheter device may further comprise a seal at the distal end to prevent back-flow of fluid, while still allowing the proboscis to be repeatedly extended and retracted. For example, the seal may be a silicon septum covering the distal opening, or one or more sealing rings within the sheath through which the proboscis is inserted. Such rings may also provide support for the proboscis and/or sheath.

The foregoing description and examples have been set forth merely to illustrate the invention and are not intended to be limiting. Each of the disclosed aspects and embodiments of the present invention may be considered individually or in combination with other aspects, embodiments, and variations of the invention. Modifications of the disclosed embodiments incorporating the spirit and substance of the invention may occur to persons skilled in the art and such modifications are within the scope of the present invention. Furthermore, all references cited herein are incorporated by reference in their entirety.

What is claimed is:

1. A catheter device having a proximal end and a distal end, comprising:
    (a) an elongated hollow housing at the distal end;
    (b) a proboscis assembly disposed within the housing, wherein the proboscis assembly has a central axis and is axially movable relative to the hollow housing; and
    (c) a transducer for measuring axial displacement of the proboscis assembly relative to the hollow housing, wherein the transducer comprises an induction coil.

2. The device of claim 1, wherein the proboscis assembly comprises a proboscis, and wherein the proboscis is disposed within the induction coil.

3. The device of claim 2, wherein the proboscis assembly is axially aligned with an axis of the induction coil.

4. The device of claim 2, wherein the proboscis assembly serves as a core for the induction coil, and wherein axial displacement of the proboscis assembly causes a change in the inductance in the induction coil.

5. The device of claim 4, wherein at least one distal portion of the proboscis assembly has a different magnetic permeability than at least one proximal portion of the proboscis assembly.

6. The device of claim 5, wherein the proboscis assembly further comprises a mounting upon which the proboscis is mounted, and wherein the mounting and the proboscis have different magnetic permeabilities.

7. The device of claim 6, wherein the proboscis and the mounting are made of different materials.

8. The device of claim 7, wherein the proboscis is made of a ferromagnetic material, and wherein the mounting is made of a non-ferromagnetic material.

9. The device of claim 6, wherein the proboscis and mounting are made of the same material, and wherein the mounting has a greater diameter than the proboscis.

10. The device of claim 1, wherein the proboscis is a needle.

11. The device of claim 1, further comprising an induction sensor coupled to the induction coil.

12. The device of claim 1, wherein the induction coil is incorporated into the hollow housing.

13. A catheter device having a proximal end and a distal end, comprising:
    (a) an elongated hollow housing at the distal end;
    (b) a proboscis assembly disposed within the housing, wherein the proboscis assembly has a central axis and is axially movable relative to the hollow housing; and
    (c) a transducer for measuring axial displacement of the proboscis assembly relative to the hollow housing, wherein the transducer comprises a potentiometer.

14. The device of claim 13, wherein the potentiometer comprises a resistor element.

15. The device of claim 14, wherein the resistor element is a coil of resistance wire.

16. The device of claim 14, wherein the resistor element is a resistance strip.

17. The device of claim 13, wherein the potentiometer is a linear potentiometer.

18. The device of claim 14, wherein the proboscis assembly comprises a contact element for electrically contacting the resistor element.

19. The device of claim 18, further comprising a resistance sensor coupled to the resistor element and the contact element.

20. The device of claim 13, wherein the proboscis is a needle.

21. A method of using a catheter device, comprising:
(i) providing a catheter device comprising:
   (a) an elongated hollow housing at the distal end;
   (b) a proboscis assembly disposed within the housing, wherein the proboscis assembly has a central axis and is axially movable relative to the hollow housing; and
   (c) a transducer for measuring axial displacement of the proboscis assembly relative to the hollow housing;
(ii) advancing the catheter device through a body lumen;
(iii) advancing the proboscis assembly; and
(iv) detecting the axial displacement of the proboscis assembly.

22. The method of claim 21, wherein the transducer comprises an induction coil.

23. The method of claim 21, wherein the transducer comprises a potentiometer.

* * * * *